United States Patent
Green et al.

(10) Patent No.: US 8,525,643 B2
(45) Date of Patent: Sep. 3, 2013

(54) MEDICAL SYSTEM WITH IDENTIFICATION PATCH

(75) Inventors: Michael T. Green, Maple Grove, MN (US); James K. Carney, Brooklyn Park, MN (US); G. Sean Haag, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 385 days.

(21) Appl. No.: 12/771,095

(22) Filed: Apr. 30, 2010

(65) Prior Publication Data

US 2011/0218408 A1    Sep. 8, 2011

Related U.S. Application Data

(60) Provisional application No. 61/309,532, filed on Mar. 2, 2010.

(51) Int. Cl.
  *G05B 23/00*    (2006.01)
(52) U.S. Cl.
  USPC .......................................... 340/5.8
(58) Field of Classification Search
  USPC ............ 340/5.8, 10.1, 505, 539.1; 600/300; 235/380, 375, 486
  See application file for complete search history.

(56) References Cited

U.S. PATENT DOCUMENTS

| | | |
|---|---|---|
| 4,546,436 A | 10/1985 | Schneider et al. |
| 5,390,675 A | 2/1995 | Sheehan et al. |
| 5,634,468 A | 6/1997 | Platt et al. |
| 5,948,006 A | 9/1999 | Mann |
| 6,200,265 B1 | 3/2001 | Walsh et al. |
| 6,482,154 B1 | 11/2002 | Haubrich et al. |
| 6,496,715 B1 * | 12/2002 | Lee et al. ...................... 600/424 |
| 6,506,155 B2 | 1/2003 | Sluis |
| 6,519,569 B1 | 2/2003 | White et al. |
| 6,605,046 B1 | 8/2003 | Del Mar |
| 6,666,821 B2 | 12/2003 | Keimel |
| 6,851,615 B2 | 2/2005 | Jones |
| 6,856,832 B1 | 2/2005 | Matsumura et al. |
| 6,945,935 B1 * | 9/2005 | Sasse et al. .................. 600/300 |

(Continued)

FOREIGN PATENT DOCUMENTS

| | | |
|---|---|---|
| EP | 1246667 B1 | 3/2005 |
| WO | 2008076464 | 6/2008 |
| WO | 2009046145 | 4/2009 |

OTHER PUBLICATIONS

Yoo et al.; "A 5.2 mW Self-Configured Wearable Body Sensor Network Controller and a 12 uW Wirelessly Powered Sensor for a Continuous Health Monitoring System"; IEEE Journal of Solid-State Circuits; vol. 45, No. 1, Jan. 2010.

(Continued)

*Primary Examiner* — Vernal Brown
(74) *Attorney, Agent, or Firm* — Stephan W. Bauer; Michael J. Ostrom

(57) ABSTRACT

A medical system that includes an identification patch having a memory that stores identification information associated with the patch. A monitoring device to be used with the identification patch interrogates the patch to obtain the identification information stored within the memory of the patch. The monitoring device determines whether the identification information is valid and, if so, measures values representing one or more parameters of the patient. If the identification information is not valid, monitoring device does not measure values representing the one or more parameters of the patient.

33 Claims, 6 Drawing Sheets

(56) References Cited

U.S. PATENT DOCUMENTS

| | | | |
|---|---|---|---|
| 6,994,249 B2 | 2/2006 | Peterka et al. | |
| 7,048,687 B1 | 5/2006 | Reuss et al. | |
| 7,152,785 B2 | 12/2006 | Metz et al. | |
| 7,333,013 B2 * | 2/2008 | Berger | 340/539.12 |
| 7,429,920 B2 | 9/2008 | Smythe et al. | |
| 7,486,977 B2 | 2/2009 | Sweitzer et al. | |
| 7,499,739 B2 | 3/2009 | Sweitzer et al. | |
| 7,616,111 B2 | 11/2009 | Covannon et al. | |
| 7,697,993 B2 * | 4/2010 | Gilkerson et al. | 607/59 |
| 2003/0083559 A1 | 5/2003 | Thompson | |
| 2004/0019288 A1 | 1/2004 | Kinast | |
| 2005/0049501 A1 | 3/2005 | Conero et al. | |
| 2005/0182389 A1 | 8/2005 | LaPorte et al. | |
| 2006/0184030 A1 | 8/2006 | Ohshima et al. | |
| 2006/0184396 A1 | 8/2006 | Dennis et al. | |
| 2007/0083111 A1 | 4/2007 | Hossack et al. | |
| 2007/0129622 A1 | 6/2007 | Bourget et al. | |
| 2007/0129769 A1 | 6/2007 | Bourget et al. | |
| 2007/0179400 A1 | 8/2007 | Dijkman | |
| 2007/0253021 A1 | 11/2007 | Mehta et al. | |
| 2008/0114220 A1 | 5/2008 | Banet et al. | |
| 2008/0161688 A1 | 7/2008 | Poland | |
| 2008/0200784 A1 | 8/2008 | Cheng | |
| 2008/0221419 A1 | 9/2008 | Furman | |
| 2008/0249379 A1 | 10/2008 | Furman | |
| 2008/0275321 A1 | 11/2008 | Furman | |
| 2008/0287800 A1 | 11/2008 | Furman | |
| 2009/0048518 A1 | 2/2009 | Furman | |
| 2009/0131761 A1 | 5/2009 | Moroney, III et al. | |
| 2009/0204019 A1 * | 8/2009 | Ginggen et al. | 600/561 |
| 2009/0209904 A1 | 8/2009 | Peeters | |
| 2009/0221882 A1 | 9/2009 | Furman | |
| 2009/0259176 A1 | 10/2009 | Yairi | |
| 2011/0237922 A1 | 9/2011 | Parker, III et al. | |

OTHER PUBLICATIONS (PCT/US2011/025664) PCT Notification of Transmittal of the International Search Report and the Written Opinion of the International Searching Authority, Mailed May 25, 2011, 9 pages.

(PCT/US2011/025660) PCT Notification of Transmittal of the International Search Report and the Written Opinion of the International Searching Authority, Mailed May 25, 2011, 8 pages.

* cited by examiner

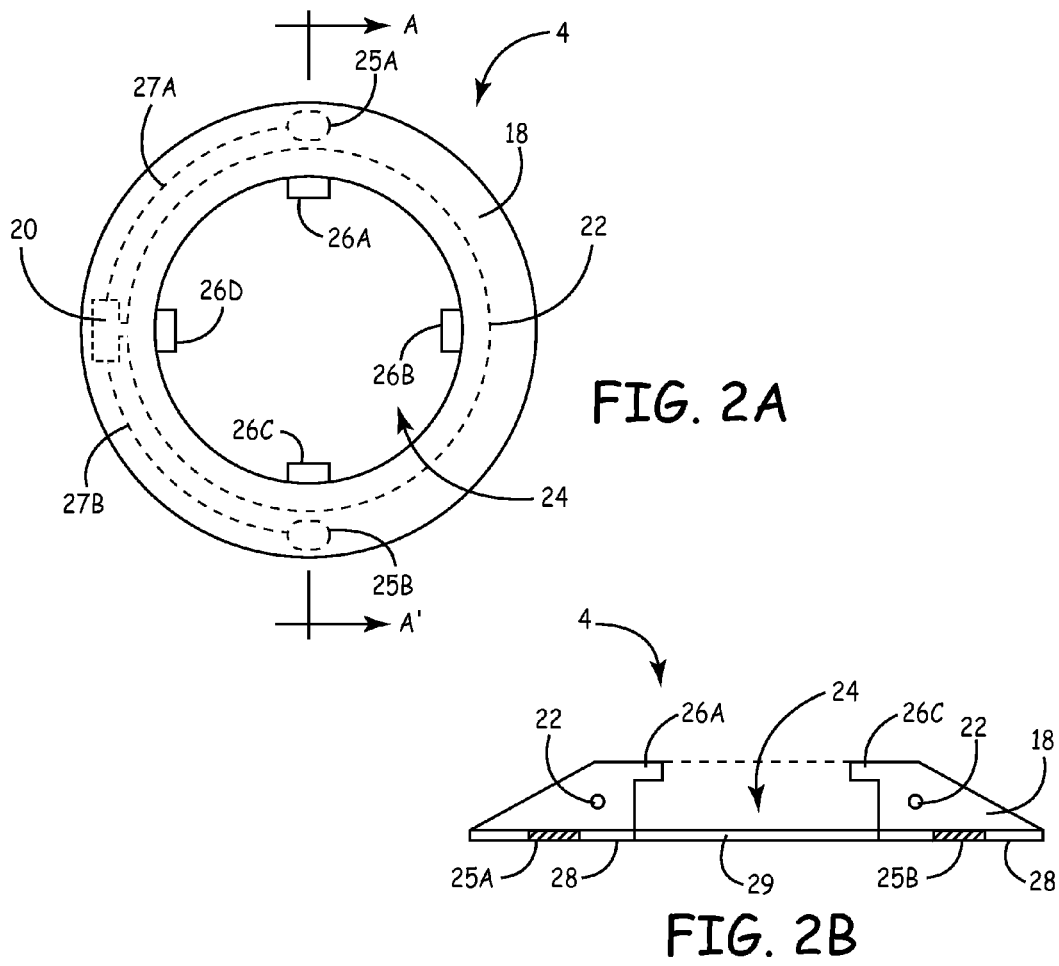
FIG. 2A
FIG. 2B
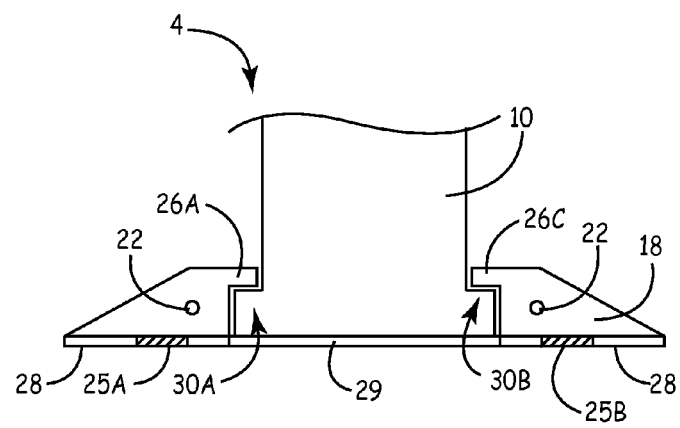
FIG. 2C

MEDICAL SYSTEM WITH IDENTIFICATION PATCH

This application claims the benefit of U.S. Provisional Application No. 61/309,532, filed on Mar. 2, 2010, which is incorporated herein by reference in its entirety.

TECHNICAL FIELD

The disclosure relates generally to devices and techniques for monitoring one or more parameters of a patient.

BACKGROUND

One or more parameters of a patient may need to be monitored over a period of time to diagnose a condition of a patient, monitor changes of the condition of the patient, to determine the efficacy of a therapy provided to the patient, or for another medical reason. In one example, a medical system may measure one or more parameters relating to cardiac performance, such as heart rate, blood flow, stroke volume, blood pressure, cardiac output, blood oxygen saturation, location and/or size of various portions of the heart, or the like. The measured parameters may be used to diagnose or monitor a cardiac condition of the patient and/or to determine a course of treatment for the cardiac condition.

SUMMARY

In general, this disclosure relates to a medical system that includes an identification patch. The identification patch is configured to be coupled to a patient and includes a memory that stores identification information associated with the patch. A monitoring device to be used with the identification patch interrogates the patch to obtain identification information stored within the memory of the patch prior to measuring values corresponding to parameters of the patient on which the patch is attached. The monitoring device determines whether the identification information is valid and, if so, measures values representing one or more parameters of the patient. If the identification information is not valid, monitoring device does not measure values representing the one or more parameters of the patient.

In one example, the disclosure is directed to a monitoring device comprising a transceiver, an antenna coupled to the transceiver, a sensor driver, a sensor coupled to the sensor driver and a processor configured to control the transceiver to transmit an interrogation signal via the antenna to a patch attached to a patient to obtain identification information of the patch, determine whether the identification information of the patch is valid, and control the sensor driver to measure at least one parameter of the patient using the sensor in response to the identification information being valid.

In another example, the disclosure is directed to a method comprising transmitting an interrogation signal from a monitoring device to a patch attached to a patient, receiving a response signal that includes identification information of the patch, determining whether the identification information of the patch is valid, and measuring at least one parameter of the patient in response to the identification information being valid.

In a further example, the disclosure is directed to a monitoring device comprising means for transmitting an interrogation signal from a monitoring device to a patch attached to a patient, means for receiving a response signal that includes identification information of the patch, means for determining whether the identification information of the patch is valid, and means for measuring at least one parameter of the patient in response to the identification information being valid.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

BRIEF DESCRIPTION OF THE DRAWINGS

FIGS. 2A-2C are schematic diagrams illustrating an example patch of the medical system of FIG. 1.

DETAILED DESCRIPTION

Figure 1:
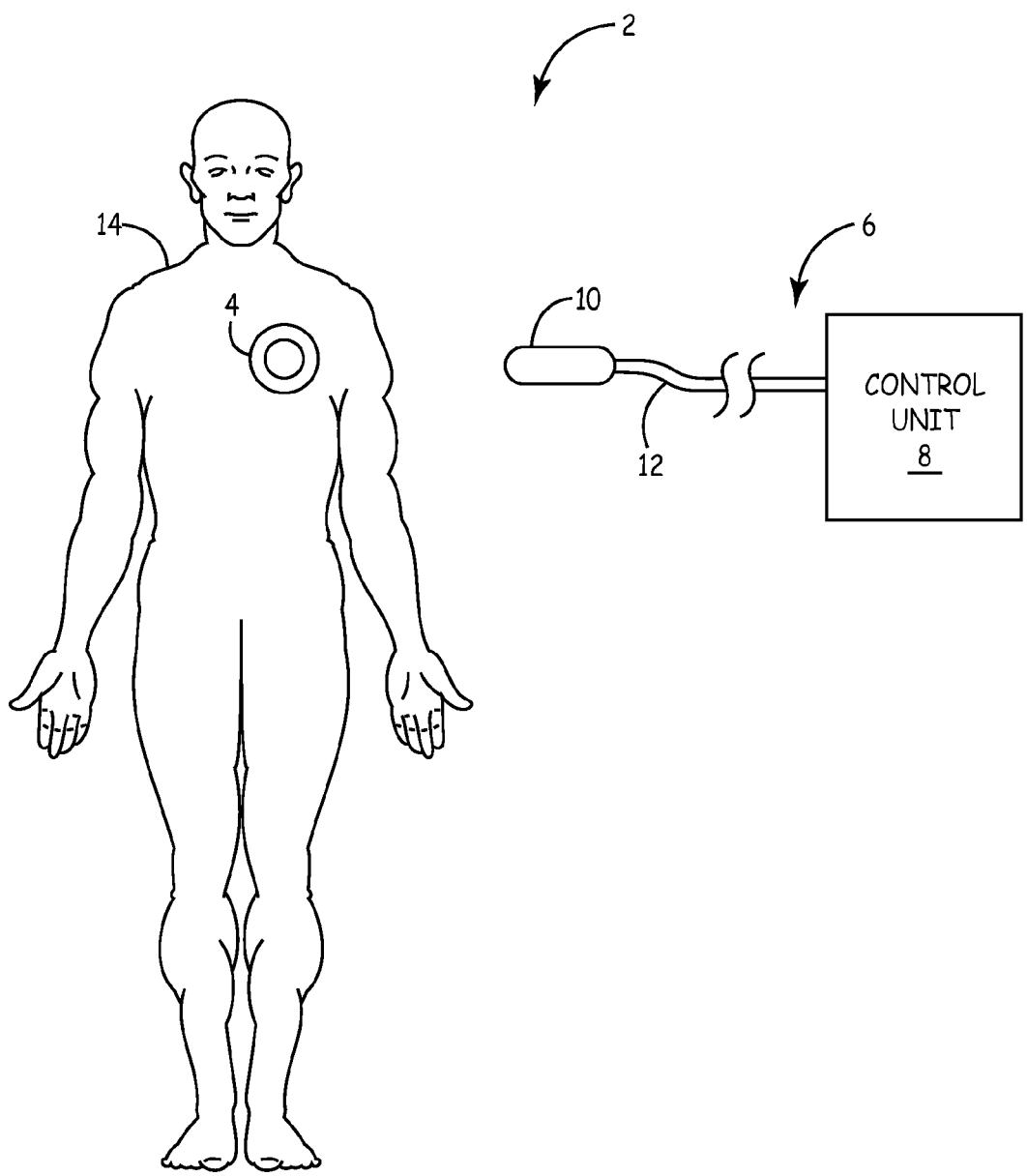
FIG. 1 is a schematic diagram illustrating a medical system for measuring one or more parameters of a patient.

FIG. 1 is a schematic diagram illustrating a medical system 2 for measuring one or more parameters of a patient 14. Medical system 2 includes a patch 4 and a monitoring device 6. In the example illustrated in FIG. 1, patch 4 is placed on a chest of patient 14 and, more particularly, over a heart of patient 14. Patch 4 may be attached to the chest of patient 14 using an attachment mechanism, such as an adhesive layer that adhesively couples patch 4 to patient 14, a strap or belt that holds patch 4 against the body of patient 14, or other attachment mechanism. Patch 4 may be placed on patient 14 upon being admitted to a hospital, arriving at an appointment, or at another appropriate time. Additionally, identification information stored within patch 4 may be associated with patient 14 when patch 4 is placed on patient 14.

Monitoring device 6 includes a control unit 8 that is coupled to a sensing probe 10 via a cable 12. Probe 10 may include one or more sensors that may be placed on patient 14 to measure values representing one or more parameters of patient 14. In the example illustrated in FIG. 1, for example, the sensors of probe 10 may measure values representing one or more parameters relating to cardiac performance. The sensors of probe 10 may be used to measure values representing parameters related to other functions in addition to or instead of cardiac performance. However, this disclosure describes the techniques with respect to monitoring parameters relating to cardiac performance for purposes of illustration and therefore should not be limited to parameters relating to cardiac function.

A user of monitoring device 6 places probe 10 on patch 4 to measure the values. In some instances, patch 4 is configured to mechanically accept a portion of probe 10. A housing of patch 4 may, for example, be constructed to form a void in the center of patch 4 that accepts the portion of probe 10. When the portion of probe 10 is placed on patch 4 within the void, a distal end of probe 10 may be in contact with the skin of patient 14. In other instances, patch 4 may include a gel-like layer between the skin of patient 14 and the distal end of probe 10. The gel-like layer between the skin of patient 14 and the distal end of probe 10 may provide for better measurement of the parameters, such as when the sensing is performed using ultrasound signals. Patch 4 and probe 10 may also include locking mechanisms that may configured to interlock with a locking mechanism of probe 10 to mechanically couple patch 4 and probe 10 upon mechanically accepting probe 10. The mechanical coupling provided by the locking mechanism may hold probe 10 steady on patient 14 and possibly even permit hands-free functionality. However, in other instances, patch 4 does not include a locking mechanism. In this case, patch 4 and probe 10 are not mechanically coupled when the portion of probe 10 is placed in the void of or mechanically accepted by patch 4.

Patch 4 includes an integrated circuit that stores identification information of patch 4. The identification information may include a unique identifier (e.g., serial number) associated with patch 4 or identification information associated with patient 14. In one example, patch 4 may include a radio frequency identification (RFID) chip with memory. Patch 4 may include other types of integrated circuits other than or in addition to the RFID chip to store the identification information. However, this disclosure will be described in the context of RFID for purposes of illustration.

After placing probe 10 on patch 4, e.g., in the void of patch 4, control unit 8 generates an interrogation signal that is transmitted by probe 10. In one example, the interrogation signal may be conducted to probe 10 via cable 12 and radiated via an antenna within probe 10. The interrogation signal may be modulated with a command requesting identification information from patch 4. Patch 4 receives the interrogation signal from probe 10 and demodulates the signal to decode the command. In addition to the command requesting identification information, the interrogation signal may include data to be stored in the memory of the integrated circuit. This data may, for example, be a timestamp indicating a time at which the interrogation signal was sent, identification information associated with monitoring device 6, identification information associated with the user of monitoring device 6, information indicating the type of sensing to be performed, or the like. Patch 4 stores this data within the memory of the integrated circuit.

In response to the interrogation signal, patch 4 sends a response signal that is modulated to include the identification information stored within the memory. As described above, the identification information may uniquely identify patch 4, patient 14 or both. In the case of a passive or semi-passive RFID chip, patch 4 sends a response signal using passive backscatter. However, patch 4 may be capable of generating and transmitting the response signal using techniques other than passive backscatter.

After sending the interrogation signal, control unit 8 monitors for a response signal from patch 4. The antenna of probe 10 receives the response signal from patch 4 and control unit 8 demodulates the response signal to decode the identification information included within the response signal. Control unit 8 determines whether the identification information is valid. In one example, control unit 8 may determine the identification information is valid when the identification information in the response signal is associated with a patient, e.g., by accessing a database that associates identification information with patient information. That database may be stored within control unit 8 or within another computing device that may be accessed by control unit 8 via wired or wireless communication (e.g., via a network such as the Medtronic CareLink® Network developed by Medtronic, Inc., of Minneapolis, Minn.). In another example, control unit 8 may determine the identification information is valid when the identification information matches a particular or expected format or has a value within a particular range.

When no response signal is received or when a response signal is received without valid identification information, monitoring device 6 does not sense the parameters of patient 14. In this manner, monitoring device 6 does not permit (e.g., prevents) the sensing of the parameters of patient 14. Instead, control unit 8 may provide an error indication to the user. The error indication may indicate that no patch has been identified or that patch 4 is not associated with a patient. When the identification information is not associated with a patient, control unit 8 may further prompt the user to enter patient information (e.g., patient's name, birth date, social security number or other patient identification information, or information associated with a condition of patient 14) to associate patch 4 with patient 14 on which patch 4 is placed. The patient information entered by the user may be stored within the database.

When the identification information is valid (e.g., is associated with a patient, has a value within a particular range, or matches a particular or expected format) or after the user has entered the patient information, control unit 8 causes monitoring device 6 to measure the one or more parameters. Monitoring device 6 may measure the one or more parameters using any of a variety of techniques. In this manner, the identification information may function to enable monitoring device 6 to measure the parameters of patient 14. In other words, control unit 8 may require that valid identification information received from patch 4 prior to measuring the parameters of patient 14.

Monitoring device 6 may measure the one or more operating parameters using an ultrasound sensor (e.g., a Doppler sensor), an optical sensor, an ECG sensor, a temperature sensor, or other sensor, or a combination of different sensors included within probe 10. The Doppler sensor emits and detects a plurality of ultrasonic waves. The optical sensor emits and detects a plurality of optical signals. The ECG sensor may detect cardiac electrical signals and the temperatures sensor may obtain body temperature measurements. Control unit 8 may process the measured values from one or more of the sensors to compute parameter values, including heart rate, blood flow, stroke volume, blood pressure, cardiac output, location and size of the portion of the heart (e.g., aorta), oxygen saturation of the blood, or the like. The example parameters are provided for purposes of illustration. Other parameters may also be computed, including parameters relating to body functions other than cardiac functions. The measure parameters may be immediately and automatically associated with patient 14 since the identification information stored on patch 4 is already associated with patient 14. The amount of user interaction is reduced by only requiring the user to enter patient information once, e.g., upon first attaching patch 4 to patient 14. Moreover, because monitoring device 6 will be used to sense parameters of a plurality of patients that each have a patch, the techniques of this disclosure further reduce the likelihood of erroneously associating the sensed medical data to the wrong patient.

The illustration in FIG. 1 is provided for exemplary purposes and should not be considered limiting of the techniques disclosed in this disclosure. For example, although in the example illustrated in FIG. 1 patch 4 is placed on the chest of patient 14, patch 4 may be placed on other locations of patient 14 based on the parameters of interest. As another example, monitoring device 6 may integrate control unit 8 and probe 10 into a common housing, e.g., by putting all the functionality of control unit 8 into hand-held probe 10.

FIGS. 2A-2C illustrate an example patch 4 from various vantage points. FIG. 2A is a perspective diagram illustrating a top view of patch 4. FIG. 2B is a sectional view of patch from taken from A to A'. FIG. 2C is a sectional view of patch 4 taken from A to A' after probe 10 is placed on patch 4.

Patch 4 includes a housing 18 that encases an integrated circuit 20 and an antenna 22. Housing 18 may provide sufficient protective qualities to integrated circuit 20 and antenna 22. Housing 18 may be a malleable, pliable, flexible device or substance that conforms to the body of patient 14 when placed on patient 14. Housing 18 may be made of any of a variety of materials, including thermoplastic material, thermoset material, or polymers, such as polyester, polystyrene, polypropylene, polyethylene, or other suitable material.

Housing 18 may be constructed to form a void 24 for receiving probe 10. Void 24 may be shaped to conform to the shape of a distal end of probe 10. In the example patch 4 illustrated in FIG. 2A, void 24 is generally cylinder shaped to mechanically accept (or receive) the distal end of probe 10. As such, patch 4 may take on an annulus or ring shape. Void 24 may be formed in any of a number of different shapes to mechanically accept particular types of probes 10.

Housing 18 may also be constructed to include protrusions 26A-26D, collectively referred to as protrusions 26. Protrusions 26 extend from the inner circumference of housing 18 into void 24. Protrusions 26 may be made of the same material as the rest of housing 18. Alternatively, protrusions 26 may be made from a different material that is not as malleable, pliable or flexible as the rest of housing 18. As illustrated in FIG. 2B, the thickness of protrusions 26 is less than the thickness of patch 4. This enables protrusions of probe 10 (described in FIG. 3) to be oriented below protrusions 26, thus mechanically coupling probe 10 to patch 4 (as illustrated in FIG. 2C). Alternatively, housing 18 may be constructed with a different attachment mechanism for interlocking with probe 10. For example, housing 18 may have a spring clip that attaches to probe 10. Any attachment mechanism may be used to mechanically couple probe 10 to patch 4 when void 24 of patch 4 mechanically accepts probe 10. In yet other instances, housing 18 may have no mechanism for mechanically coupling patch 4 to probe 10. In this case, probe 10 is not locked into place when void 24 of patch 4 mechanically accepts probe 10.

With further reference to FIG. 2B, patch 4 may include an adhesive layer 28 on a bottom side of housing 18 (i.e., the side to be attached to patient 14). Adhesive layer 28 may include a pressure sensitive adhesive. In other instances, patch 4 may include a strap or belt that attaches patch 4 to the body of patient 14.

Patch 4 may also include a gel-like layer 29 in a bottom of void 24 at the skin-patch interface. For example, patch 4 may include gel-like layer 29 when probe 10 uses a Doppler sensor to sense the one or more parameters using ultrasound signals. Gel-like layer 29 may be formed of a material similar to that used in ultrasound gels. Gel-like layer 29 may remove air between the skin of patient 14 and the Doppler sensor of probe 10 so that the ultrasound signals may be efficiently coupled between the body of patient 14 and the Doppler sensor. In instances in which patch 4 does not include gel-like layer 29, the distal end of sensing probe 10 is in direct contact with the skin of patient 14 when placed within the void of the patch.

Patch 4 may also include two or more electrodes, such as electrodes 25A and 25B that make contact with the skin of patient 14. Electrodes 25A and 25B may be used to sense cardiac electrical activity of patient 14. Electrodes 25A and 25B may be electrically coupled to integrated circuit 20 via conductors 27A and 27B, respectively. In this case, integrated circuit 20 may include circuitry to process the signals sensed by electrodes 25A and 25B to measure a physiological signal of patient 14, such as an electrocardiogram (ECG). Integrated circuit 20 may store the sensed and/or processed data. Integrated circuit 20 may also convert the sensed and/or processed data to a digital signal for transmission to the monitoring device 6 via antenna 22. Alternatively, electrodes 25A and 25B may be coupled to an electrical connector that electrically couples to probe 10 of monitoring device 6 when probe 10 is placed within void 24. In this case, measurement of the ECG or other parameter may be performed by circuitry in monitoring device 6.

In the example illustrated in FIG. 2A, antenna 22 is a loop antenna. Antenna 22 includes a conductor (e.g., wire or conductive trace) that is formed into a single loop. The loop of antenna 22 generally follows the shape of patch 4. In the example of patch 4, the loop of antenna 22 is a circle. The loop of antenna 22 may be other shapes, such as a square loop, oval loop, triangular loop or other shape, and may depend on the overall shape of the patch. Moreover, antenna 22 may include more than one loop. In other instances, patch 4 may include an antenna that is not a loop antenna, such as a monopole antenna, dipole antenna, whip antenna or any other type of antenna.

Integrated circuit 20 includes a memory or is coupled to a separate memory that stores identification information of patch 4. The memory may, for example, store a unique serial number associated with patch 4. The memory may store additional data, such as information associated with patient 14, information received from probe 10, or information generated by integrated circuit 20. Integrated circuit 20 may further be capable of demodulating signals received by antenna 22 and modulating signals for transmission by antenna 22. For example, integrated circuit 20 may demodulate an interrogation signal received from probe 10 to decode a command, perform the command (e.g., retrieve identification information) and modulate a response signal to include the identification information. In some instances, integrated circuit 20 may be capable of performing other specialized functions, such as maintaining a counter or tracking an amount of time to perform the functions described in further detail below.

Patch 4 may include indicia to aid in the placement of patch 4 on patient 14 or to aid in the interlocking or mechanical coupling of patch 4 with probe 10. Patch 4 may, for example, include an arrow, triangle or other marking on the side of patch 4 not placed on patient 14. The indicia may indicate the orientation with which patch 4 should be placed on patient, e.g., with the arrow pointing toward a head of patient 12. In other instances, the indicia may be aligned with a similar indicia located on probe 10 to aid in orienting probe 10 with respect to patch 4 to improve communication with patch 4 or to assist with the interlocking or mechanical coupling of probe 10 and patch 4.

Figure 3A:
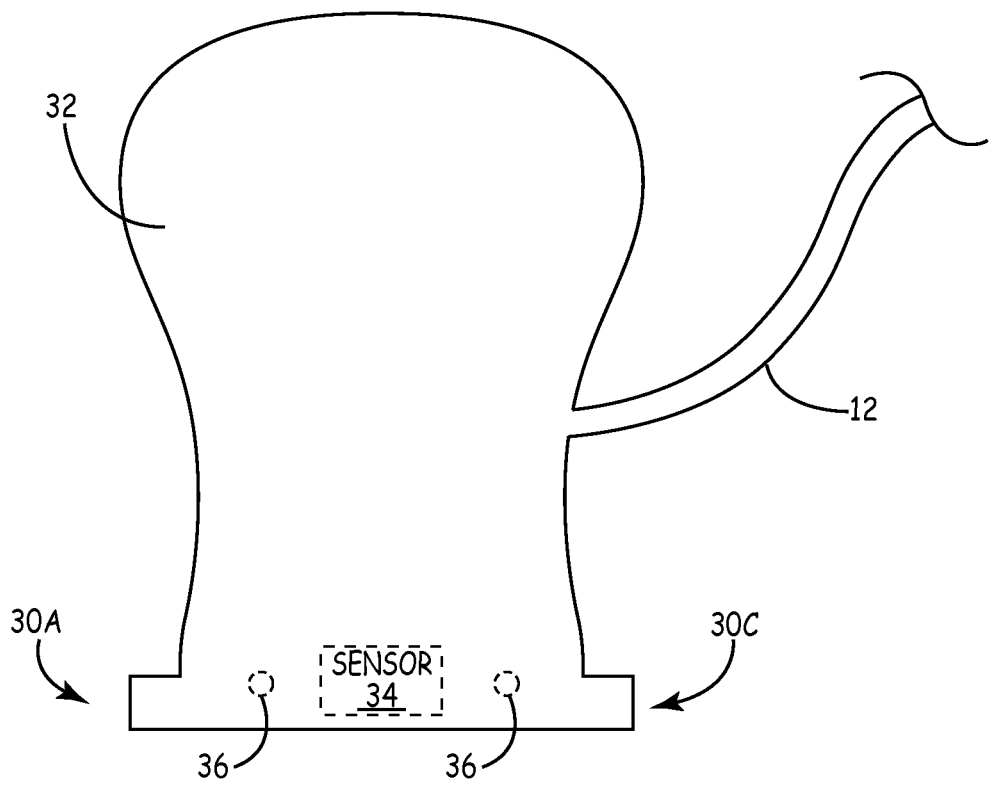
FIGS. 3A and 3B illustrate an example probe of a monitoring device of the medical system of FIG. 1.
Figure 3B:
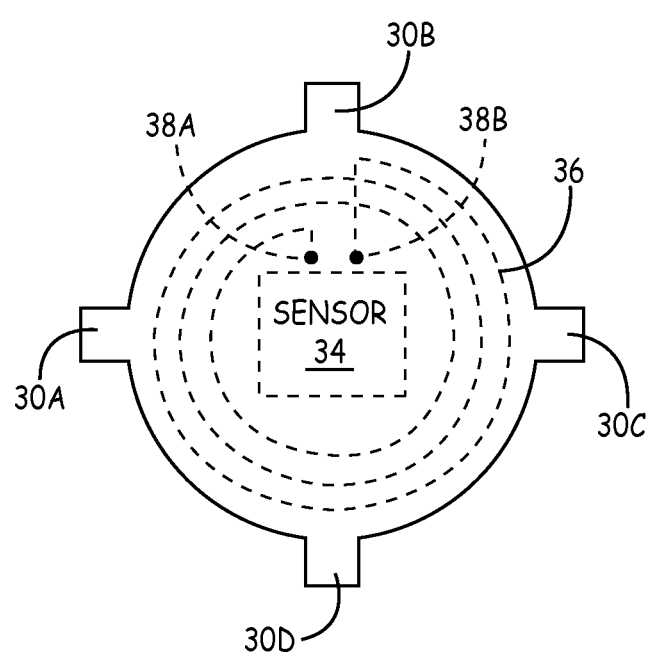

FIGS. 3A and 3B illustrate an example probe 10 of monitoring device 6. FIG. 3A illustrates a perspective view of a front of probe 10 and FIG. 3B illustrates a perspective view of a bottom of probe 10. Probe 10 includes a housing 32 that encases at least one sensor 34 and an antenna 36. Housing 32 may be constructed to form a handle for the user. Housing 32 may be formed to include protrusions 30A-30D, collectively protrusions 30, that extend outward from an outer circumference of the bottom of probe 10. The user of probe 10 may align protrusions 30 of probe 10 such that they do not overlap with protrusions 26 of patch 4, place the distal end of probe 10 (e.g., the end with the protrusions in the example of FIG. 3) within void 24 of patch 4, and turn the distal end of probe 10 such that protrusions 30 and protrusions 26 overlap, thereby mechanically coupling probe 10 in place. As described above with respect to FIGS. 2A-2C, probe 10 may include other locking mechanisms that may mate with respective locking mechanisms on patch 4 to mechanically couple patch 4 to probe 10.

Antenna 36 is a loop antenna with a plurality of loops that extend around the periphery of the bottom of probe 10. Antenna 36 includes a conductor (e.g., wire or conductive trace) that is formed into the plurality of loops. The loops of antenna 36 generally follow the shape of the bottom portion of probe 10. In the example of probe 10, the loop of antenna 36 is a circle. The loop of antenna 36 may be other shapes, such as a square loop, oval loop, triangular loop or other shape, and may depend on the overall shape of the bottom portion of probe 10. Moreover, antenna 36 may include more or fewer loops. In other instances, probe 10 may include an antenna that is not a loop antenna, such as a monopole antenna, dipole antenna, whip antenna or any other type of antenna.

As will be described in more detail below, antenna 36 may be used to transmit interrogation signals to and receive response signals from patch 4 to obtain identification information associated with patch 4 and/or patient 14. The transmitted and received signals may be conducted from and to control unit 8 via conductors extending along cable 12 and coupled to antenna 36 via contact points 38A and 38B. As described above, probe 10 may be a handheld device that includes control unit 8 within housing 32 of probe 10 and coupled to antenna 36 via conductors within housing 32.

Sensor 34 measures values representing one or more parameters of patient 14. Sensor 34 may be controlled to sense the parameters after control unit 8 receives valid identification information (e.g., identification information that is associated with a patient, has a value within a particular range, or matches a particular or expected format) from patch 4 as described in detail herein. Sensor 34 may be coupled to a sensor driver within control unit 8 of monitoring device 6 via one or more conductors extending along cable 12. Alternatively, the sensor driver may be included within housing 32 of probe 10 (e.g., in the case of a cordless, handheld probe) and coupled to sensor 34 via conductors within housing 32.

Sensor 34 may be any of a variety of sensors or combination of different sensors, including an ultrasound (e.g., Doppler sensor), an optical sensor, an ECG sensor, or a temperature sensor. In the case of the Doppler sensor, sensor 34 may include an array of transducers to transmit ultrasonic waves and to receive reflected ultrasonic waves. Some example Doppler sensors are described in U.S. Patent Pub. No. 2008/0287800, entitled, "DOPPLER MOTION SENSOR APPARATUS AND METHOD OF USING SAME," (referred to herein as the "the Doppler sensor application") which was filed May 12, 2009 and which is incorporated herein by reference for the description of the Doppler sensors and their operation.

In the case of the optical sensor, sensor 34 may include an array of optoelectronic devices that emit optical signals into the body of patient 14 and detect optical signals reflected from portions of the body patient 14. The array of optoelectronic devices may include, for example, an array of photodiodes, phototransistors, photomultipliers, photoresistors, light emitting diodes, diode lasers, integrated optical circuits, or other optoelectronic devices or a combination of different optoelectronic devices. Some example optical sensors are described in U.S. Patent Pub. No. 2008/0275321, entitled, "OPTICAL SENSOR APPARATUS AND METHOD OF USING SAME," (referred to herein as the "the optical sensor application") which was filed May 12, 2008 and which is incorporated herein by reference for the description of the optical sensors and their operation.

Figure 4:
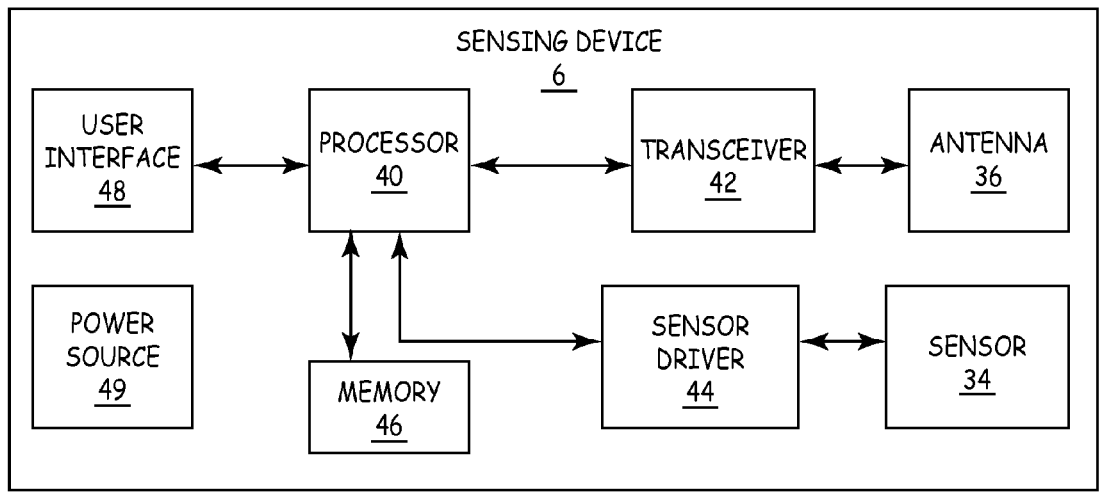
FIG. 4 is a block diagram illustrating components of a monitoring device.

FIG. 4 is a block diagram illustrating components of an example monitoring device 6. Monitoring device 6 includes a processor 40, transceiver 42, antenna 36, sensor driver 44, sensor 34, memory 46, user interface 48, and power source 49. The components of monitoring device 6 may be distributed between control unit 8 and probe 10. In one example, sensor 34 and antenna 36 may be incorporated within probe 10 while the rest of the components are incorporated within control unit 8. In another example, all the components of monitoring device 6 may be incorporated within probe 10.

Processor 40 controls operation of monitoring device 6. Processor 40 may include one or more microprocessors, digital signal processors (DSPs), application specific integrated circuits (ASICs), field-programmable gate arrays (FPGAs), programmable logic circuitry, or the like, that may perform various functions and operations, such as those described herein. Processor 40 may execute computer-readable instructions stored within memory 46 to cause one or more of the components of monitoring device 6 to perform various functions attributed to those components in this disclosure. Memory 46 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other computer-readable storage media.

Processor 40 controls transceiver 42 to generate an interrogation signal that is transmitted by antenna 36. Processor 40 may control transceiver 42 to generate and transmit the interrogation signal upon receiving an input from the user, such as actuation of a button on probe 10. Alternatively, processor 40 may control transceiver 42 to generate and transmit the interrogation signal upon receiving an input from a sensor, such as a sensor on the distal end of probe 10 that detects that probe 10 has been placed on or within patch 4. Transceiver 42 may modulate a carrier signal with a command requesting identification information from patch 4. In one example, transceiver 42 may be an RFID transceiver that generates an RF signal for transmission via antenna 36. Transceiver 42 may generate RF signals in any of a number of frequency ranges, including at low frequencies (e.g., less than 135 kHz), medium frequencies (e.g., between 3 and 28 MHz and particularly 13.5 MHz), ultra high frequencies (UHF) (e.g., 400-900 MHz), or super high frequencies (e.g., 2.4 GHz or above). Transceiver 42 also demodulates signals received via antenna 36, e.g., response signals from patch 4, to decode the identification information included within the received signal. Monitoring device 6 may transmit communications to and receive communications from patch 4 via other communication techniques, including inductive coupling, capacitive coupling, electrical coupling, electromagnetic coupling, magnetic coupling, acoustic coupling, or any other communicative coupling.

Processor 40 determines whether the identification information is valid. In another example, processor 40 may determine whether the identification information is valid when the identification information matches a particular format or has a value within a particular range. In another example, processor 40 may determine whether the identification information is valid when the identification information in the response signal is associated with a patient. Processor 40 may access a database that associates identification information with patient information. In some instances, the database may be stored in memory 46 of monitoring device 6. In other instances, monitoring device 6 may access the database on a remote computing device, e.g., via wired or wireless communication. To this end, monitoring device 6 may include a communication module (not shown) capable of communicating with the remote computing device. When the identification information is not associated with a patient, processor 40 may prompt the user via an output mechanism, such as a display (e.g., a cathode ray tube (CRT) display, a liquid crystal display (LCD) or light emitting diode (LED) display) or speaker, of user interface 48 to enter information related to patient 14 on which patch 4 is placed. The user may enter the patient information via an input mechanism, such as a keypad, a peripheral pointing device, a touch screen, microphone or the like, of user interface 48. Processor 40 may store the identification information associated with patch 4 and the patient information entered by the user within memory 46.

When the identification information is valid (e.g., is associated with a patient, has a value within a particular range, or matches a particular or expected format) or after the user of monitoring device 6 has entered the patient information, processor 40 controls sensor driver 44 to sense one or more parameters of patient 14 using sensor 34. Sensor driver 44 produces a signal to drive sensor 34 to transmit an ultrasound signal, an acoustic signal, an optical signal, or other signal into the body of patient 14. In the case of ultrasound, sensor driver 44 may drive sensor 34 with a continuous wave signal or a pulsed wave signal. In instances in which sensor 34 includes an array of elements (e.g., transducers or optoelectric elements), sensor driver 44 may drive different ones of the elements with different frequency signals. Such a technique is described in further detail for a Doppler sensor in the Doppler sensor application referenced above and for an optical sensor in the optical sensor application, both of which were incorporated above for their respective descriptions of the sensors.

Processor 40 may also process the signals detected by sensor 34 to obtain values for the one or more parameters of patient 14. In the case of the Doppler sensor, processor 40 may estimate velocity of a fluid of interest by directing an ultrasound signal of ultrasonic energy towards the fluid at a known angle, measuring the frequency shift of the reflected ultrasound energy, and then calculating the velocity of the fluid. The Doppler frequency shift is proportional to the component of the velocity vector that is parallel to the ultrasound signal. The velocity v of the fluid is determined by the following equation:

$$v = f_d \cdot c / (2 \cdot f \cdot \cos \theta)$$

where c is the velocity of sound in blood, f is the frequency of the ultrasound signal, θ is the incident angle (i.e., angle between the ultrasound signal and the velocity vector that is parallel to the ultrasound signal), and $f_d$ is Doppler frequency shift.

The Doppler frequency shift may be calculated by a variety of methods depending on the method of operation of the transducer(s) of sensor 34. In the case of a continuous wave Doppler sensor that includes a transducer for transmitting ultrasound signal and a transducer for receiving ultrasound signal, the frequency shift is measured directly by comparing the two signals. In the case of a pulsed wave Doppler sensor, which has a single transducer for transmitting and receiving ultrasound signals, the Doppler sensor switches to a receiving mode of operation after transmitting an ultrasound signal and determines the frequency shift by comparing phase shifts between subsequently received signals. A plurality of signals transmitted and received in sequence are necessary to calculate the phase shifts in the case of a pulsed wave Doppler sensor. Well known algorithms, such as the Kasai or the cross-correlation algorithms, may be used to obtain the phase shift between the received and transmitted pulses.

The incident angle (θ) or other data characterizing the relative position of the vessel with respect to sensor 34 may be obtained in various ways. Once obtained, the relative position data may be stored in memory 46 for future reference. In one embodiment, the incident angle or other relative position data may be input by a user. In another embodiment, the incident angle or other relative position data may be determined using another sensor, such as the optical sensor described in the optical sensor application, which is incorporated herein by reference for its description regarding vessel detection.

As described in this disclosure, processor 40 may require that valid identification information be received from patch 4 prior to measuring values representative of the one or more parameters of patient 14 with sensor 34. In this manner, the identification information may function to unlock monitoring device 6 to measure the values of the parameters of patient 14. Monitoring device 6 may not permit (e.g., prevents) the sensing of the parameters of patient 14 in the case of invalid identification information. The amount of user interaction is reduced by only requiring the user to enter patient information once, e.g., upon first attaching patch 4 to patient 14. Moreover, because monitoring device 6 will be used to sense parameters of a plurality of patients that each have a patch, the techniques of this disclosure reduce the likelihood of erroneously associating the sensed medical data to the wrong patient.

The various components of monitoring device 6 are powered by power source 49. Power source 49 may hold a limited amount of power, e.g., in the case of a rechargeable or non-rechargeable battery. Alternatively, power source 49 may include a power cord or cable that plugs into an alternating current (AC) source (e.g., a wall outlet) and thus have unlimited power.

Although FIGS. 1-4 are described in the context of wireless communicative coupling, e.g., RF, inductive or the like, the techniques of this disclosure may also utilize electrical coupling. For example, patch 4 and probe 10 may each include an electrical connector that couple to one another to electrically couple the medical system to the patch. In this manner, the electrical connector may communicatively couple component(s) of monitoring system 6 to integrated circuit 20 and/or memory 50. The electrical connectors may, for example, comprise conductive pads located on one or more of the protrusions 26 and 30 and contact one another when probe 10 is placed in void 24 of probe 10. Instead of a conductive pad, the electrical connectors may be conductive traces that extend around the inner circumference of void 24 and the distal end of probe 10, respectively. Other electrical connectors are also contemplated. In these examples, monitoring device 6 may interrogate patch 4 via the electrical coupling. Additionally, monitoring device 6 may provides power to one or more components (e.g., integrated circuit 20) of patch 4 via the electrical coupling.

Figure 5:
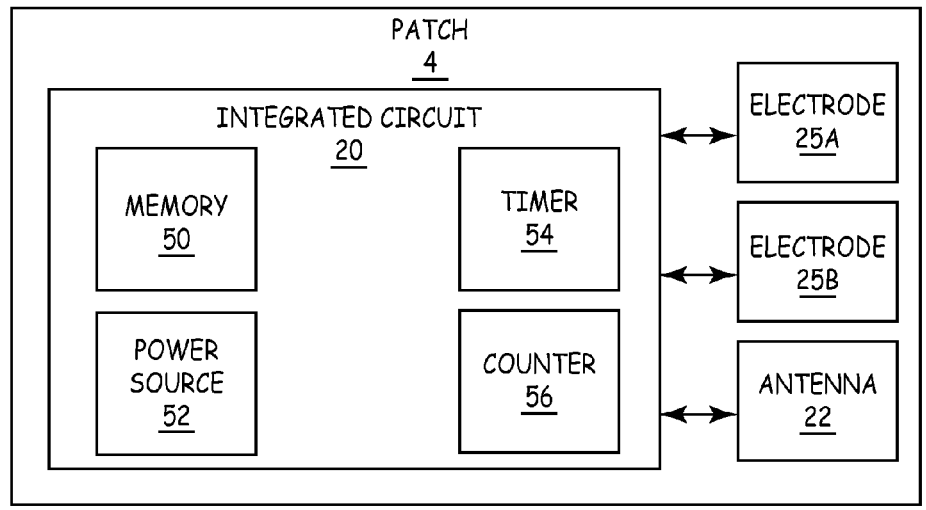
FIG. 5 is a block diagram illustrating components of an example patch.

FIG. 5 is a block diagram illustrating components of an example patch 4. Patch 4 includes an integrated circuit 20, an antenna 22, electrodes 25A and 25B, and a power source 52. Power source 52 provides power to integrated circuit 20 or any other components of patch 4. Power source 52 may be a rechargeable or non-rechargeable battery or a power-harvesting device that harvests power from the interrogation signal.

Integrated circuit 20 includes a memory 50, a timer 54 and a counter 56. Memory 50 stores identification information associated with patch 4, patient 14 or both. In one example, memory 50 may store a unique identification number associated with patch 4. Memory 50 may store other information, such as information associated with patient 14, information received from probe 10 (e.g., information associated with probe 10, a user of probe 10, timestamps, or the like), or information generated by integrated circuit 20. Memory 50 may include any volatile, non-volatile, magnetic, optical, or electrical media, such as RAM, ROM, NVRAM, SRAM, EEPROM, flash memory, or any other computer-readable storage media. In the example illustrated in FIG. 5, memory 50 is internal memory of integrated circuit 20. In other instances, however, memory 50 may be a separate memory external to integrated circuit 20 or a combination of internal and external memory.

In response to receiving an interrogation signal, integrated circuit 20 causes patch 4 to transmit a response signal that includes the identification information. Integrated circuit may also maintain a timer 54 and/or a counter 56. Timer 54 may track the amount of time that has elapsed since receiving the first interrogation signal or track the amount of time between interrogations. Counter 56 may track the number of times that patch 4 receives an interrogation signal. In other embodiments, integrated circuit 20 may not maintain time 54 or counter 56. When integrated circuit does maintain timer 54 or counter 56 or maintains some other sort of information in addition to the identification information, the response signal transmitted by patch 4 may include the additional information. For example, the response signal transmitted by patch 4 may include a current value of timer 54 and/or a current value of counter 56 maintained by integrated circuit 20.

As described above, electrodes 25A and 25B may be used to sense cardiac electrical activity of patient 14 and provide the sensed data to integrated circuit 20. Integrated circuit 20 may include circuitry to process the signals sensed by electrodes 25A and 25B to measure an electrocardiogram (ECG) or other parameter of patient 14. Integrated circuit 20 may store the sensed and/or processed data in memory 50. Integrated circuit 20 may also convert the sensed and/or processed data to a digital signal for transmission to the monitoring device 6 via antenna 22.

Figure 6:
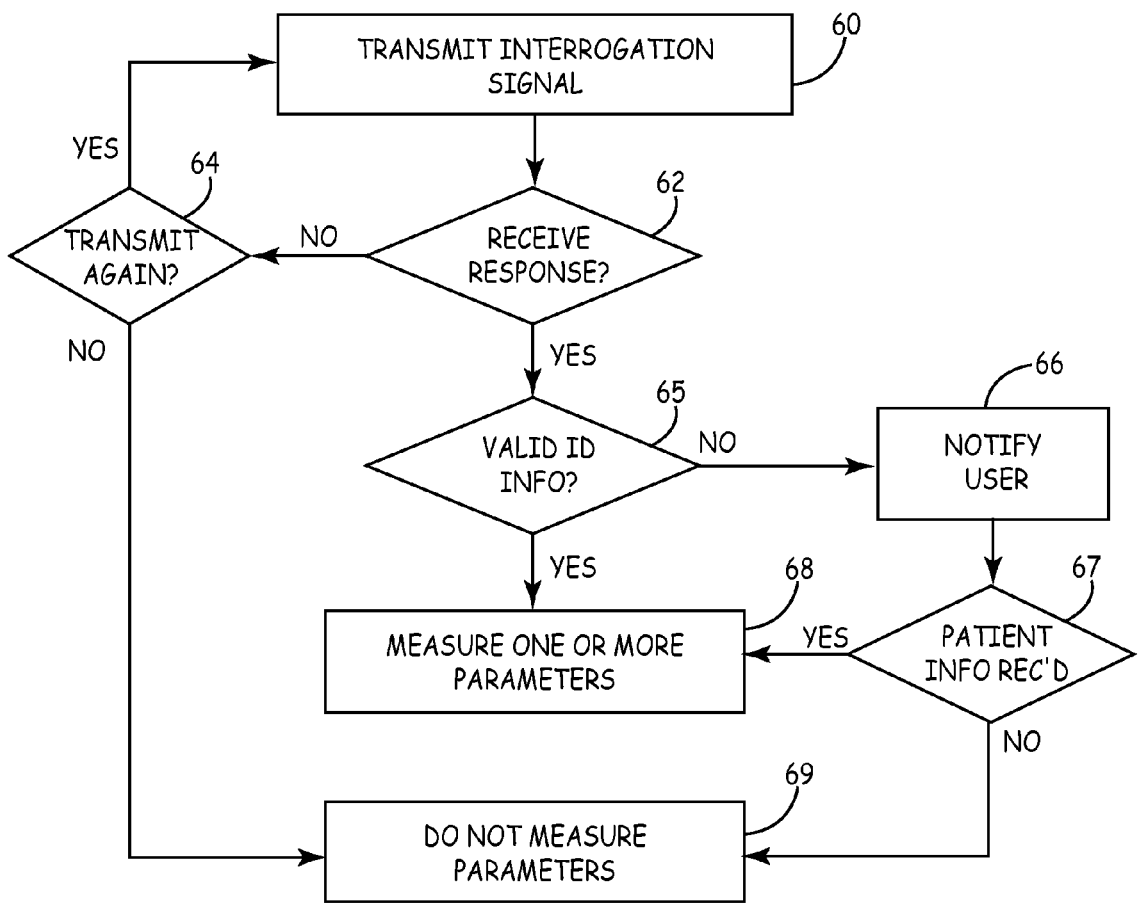
FIG. 6 is a flow diagram illustrating example operation of a monitoring device in accordance with one aspect of this disclosure.

FIG. 6 is a flow diagram illustrating example operation of a monitoring device 6 in accordance with one aspect of this disclosure. Processor 40 of monitoring device 6 controls transceiver 42 to transmit an interrogation signal via antenna 36 (60). Processor 40 may control transceiver 42 to transmit the interrogation signal in response to input from a user or in response to determination that probe 10 has been placed within patch 4. After sending the interrogation signal, processor 40 monitors for a response signal from a patch, such as patch 4 (62).

When processor 40 does not receive a response signal within a predetermined period of time ("NO" branch of block 62), processor 40 determines whether to transmit another interrogation signal (64). Processor 40 may be configured to continue transmitting interrogation signals for a particular period of time or may be configured to transmit a particular number of interrogation signals. To this end, processor 40 may maintain an interrogation timer that tracks the amount of time since the first interrogation signal was transmitted or maintain an interrogation counter that tracks the number of interrogation signals that have been transmitted. When processor 40 determines to transmit another interrogation signal, e.g., the interrogation timer has not expired or the interrogation counter has not reached a threshold value ("YES" branch of block 64), processor 40 controls transceiver 42 to transmit another interrogation signal via antenna 36 and monitor for a response signal. When processor 40 determines to not transmit another interrogation signal, e.g., the interrogation timer has expired or the interrogation counter has reached the threshold value ("NO" branch of block 64), monitoring device 6 does not measure values representing the one or more parameters of patient 14.

When processor 40 does receive a response ("YES" branch of block 62), processor 40 determines whether identification information contained in the response is valid (65). Processor 40 may determine that the identification information is valid when the identification information is associated with a patient, has a value within a particular range, or matches a particular or expected format. When the identification information contained in the response is valid ("YES" branch of block 65), monitoring device 6 measures values representing one or more parameters of patient 14 using sensor 34 (68). As described above, sensor 34 may transmit and receive a plurality of signals (such as ultrasound and or optical signals) and processor 40 may process the received signals to estimate the one or more parameters of patient 14.

When the identification information contained in the response is not valid ("NO" branch of block 65), processor 40 notifies a user of monitoring device 6 that no valid identification information has been detected (66). The notification to the user of monitoring device 6 may further prompt the user to enter patient information for the patient on which patch 4 is affixed. After receiving patient information from the user ("YES" branch of block 67), monitoring device 6 measures values representing one or more parameters of patient 14 using sensor 34 (68). When no patient information is received from the user when prompted ("NO" branch of block 67), monitoring device 6 does not measure values representing the one or more parameters (69). In this manner, the identification information may function to unlock monitoring device 6 to measure values representing the parameters of patient 14.

Figure 7:
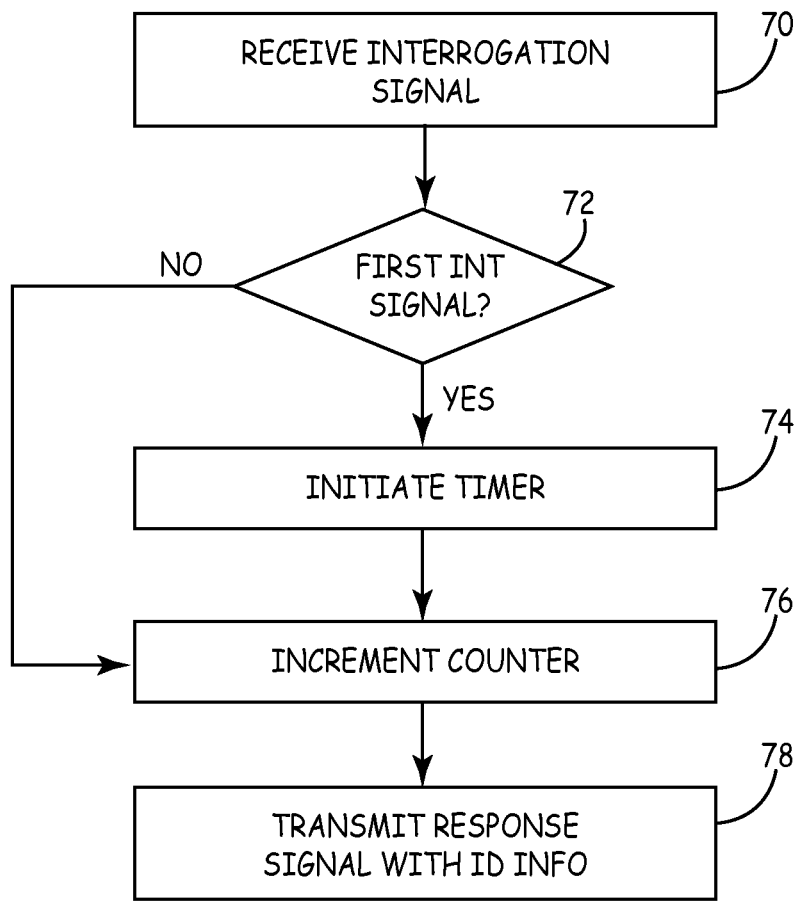
FIG. 7 is a flow diagram illustrating example operation of a patch in accordance with one aspect of this disclosure.

FIG. 7 is a flow diagram illustrating example operation of patch 4 in accordance with one aspect of this disclosure. Integrated circuit 20 of patch 4 receives an interrogation signal from probe 10 via antenna 22 (70). Integrated circuit 20 determines whether the interrogation signal is the first interrogation signal patch 4 has received (72). When integrated circuit 20 determines that the interrogation signal is the first interrogation signal patch 4 has received ("YES" branch of block 72), integrated circuit 20 may initiate a timer (74). The timer may track the amount of time that has elapsed since receiving the first interrogation signal or track the amount of time between interrogations. After initiating the timer or when integrated circuit 20 determines that the interrogation signal is not the first interrogation signal patch 4 has received ("NO" branch of block 72), integrated circuit 20 may increment a counter that tracks the number of times that patch 4 receives an interrogation signal (76).

As described above, the interrogation signal from probe 10 includes a command to retrieve identification information. In response to the command in the interrogation signal, integrated circuit 20 causes patch 4 to transmit a response signal with the identification information (70). The response signal may also include a current value of the timer and/or the counter maintained by integrated circuit 20. Although in the example of FIG. 7, integrated circuit 20 maintains a timer and a counter, integrated circuit 20 may maintain the timer without maintaining the counter or maintain the counter without maintaining the timer. Additionally, integrated circuit 20 may track other sorts of information regarding the interrogation of patch 4, including the amount of time between interrogations, identification information associated with the monitoring device 6, identification information associated with a user of monitoring device 6, or the like.

The techniques described in this disclosure, including those attributed to patch 4 and monitoring device 6, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, SRAM, EEPROM, flash memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A monitoring device comprising:
a transceiver;
an antenna coupled to the transceiver;
a sensor driver;
a sensor coupled to the sensor driver; and
a processor configured to control the transceiver to transmit an interrogation signal via the antenna to a patch attached to a patient to obtain identification information of the patch, determine whether the identification information of the patch is valid, and control the sensor driver to measure at least one parameter of the patient using the sensor in response to the identification information being valid.

2. The monitoring device of claim 1, wherein the processor is configured to not permit measurement of the at least one parameter when the identification information is not valid.

3. The monitoring device of claim 1, wherein the processor determines whether the identification information of the patch is associated with the patient and determines the identification information is valid when the identification information is associated with the patient.

4. The monitoring device of claim 3, further comprising a memory that stores a database that associates identification information with corresponding patients, wherein the processor accesses the database to determine whether the identification information of the patch is associated with the patient.

5. The monitoring device of claim 3, further comprising a user interface, wherein the processor is configured to prompt a user of the monitoring device via the user interface when the identification information is not associated with the patient, receive patient information from the user via the user interface, and control the sensor driver to measure at least one parameter of the patient using the sensor upon receiving the patient information.

6. The monitoring device of claim 1, wherein the processor determines the identification information is valid when the identification information matches an expected format or has a value within a particular range.

7. The monitoring device of claim 1, further comprising a sensing probe that houses at least the sensor and the antenna, wherein at least a portion of the sensing probe is configured to be placed within a void of the patch.

8. The monitoring device of claim 7, further comprising a control unit that houses at least the transceiver, the sensor driver and the processor, wherein the control unit is coupled to the sensing probe via a cable.

9. The monitoring device of claim 7, wherein the sensing probe houses the transceiver, the sensor driver and the processor.

10. The monitoring device of claim 1, further comprising a locking mechanism that is configured to mechanically couple the monitoring device to the patch.

11. The monitoring device of claim 1, wherein the processor is configured to transmit information within the interrogation signal.

12. The monitoring device of claim 11, wherein the information within the interrogation signal includes at least one of a timestamp indicating a time at which the interrogation signal was sent, identification information associated with the monitoring device, identification information associated with a user of the monitoring device, and information indicating the type of sensing to be performed.

13. The monitoring device of claim 1, wherein the antenna comprises a conductor arranged to form one or more loops.

14. The monitoring device of claim 1, wherein the monitoring device is configured to monitor at least one hemodynamic parameter of the patient.

15. The monitoring device of claim 1, wherein the sensor comprises at least one of an ultrasound sensor, optical sensor, electrocardiogram sensor, or temperature sensor.

16. A method comprising:
transmitting an interrogation signal from a monitoring device to a patch attached to a patient;
receiving a response signal that includes identification information of the patch;
determining whether the identification information of the patch is valid; and
measuring, with the monitoring device, at least one parameter of the patient in response to the identification information being valid.

17. The method of claim 16, further comprising preventing measurement of the at least one parameter when the identification information is not valid.

18. The method of claim 16, wherein determining whether the identification information of the patch is valid comprises:
determining whether the identification information of the patch is associated with the patient; and
determining that the identification information is valid when the identification information is associated with the patient.

19. The method of claim 18, further comprising storing a database that associates identification information with corresponding patients, wherein the determining whether the identification information of the patch is associated with the patient comprises accessing the database to determine whether the identification information of the patch is associated with the patient.

20. The method of claim 18, further comprising:
prompting a user of the monitoring device via a user interface when the identification information is not associated with the patient;
receiving patient information from the user via the user interface; and
measuring the at least one parameter of the patient upon receiving the patient information.

21. The method of claim 16, wherein determining whether the identification information of the patch is valid comprises determining that the identification information is valid when the identification information matches an expected format or has a value within a particular range.

22. The method of claim 16, further comprising constructing a portion of the monitoring device such that the portion of the monitoring device is configured to be placed within a void of the patch.

23. The method of claim 16, further comprising mechanically coupling the monitoring device to the patch via a locking mechanism.

24. The method of claim 16, further comprising transmitting information within the interrogation signal.

25. The method of claim 24, wherein the information within the interrogation signal includes at least one of a timestamp indicating a time at which the interrogation signal was sent, identification information associated with the monitoring device, identification information associated with a user of the monitoring device, and information indicating the type of sensing to be performed.

26. The method of claim 16, wherein measuring at least one parameter of the patient comprises measuring at least one hemodynamic parameter of the patient.

27. The method of claim 16, wherein measuring at least one parameter of the patient comprises measuring at least one parameter of the patient using at least one of ultrasound signals and optical signals.

28. A monitoring device comprising:
means for transmitting an interrogation signal from a monitoring device to a patch attached to a patient;
means for receiving a response signal that includes identification information of the patch;
means for determining whether the identification information of the patch is valid; and
means for measuring at least one parameter of the patient in response to the identification information being valid.

29. The monitoring device of claim 28, wherein the measuring means prevent measurement of the at least one parameter when the identification information is not valid.

30. The monitoring device of claim 28, means for generating the interrogation signal to include at least one of a timestamp indicating a time at which the interrogation signal was sent, identification information associated with the monitoring device, identification information associated with a user of the monitoring device, and information indicating the type of sensing to be performed.

31. The monitoring device of claim 28, further comprising means for communicatively coupling the monitoring device to the patch.

32. The monitoring device of claim 31, wherein the means for communicatively coupling the monitoring device to the patch comprises an antenna.

33. The monitoring device of claim 31, wherein the means for communicatively coupling the monitoring device to the patch comprises an electrical connector.

* * * * *